US009737267B2

(12) United States Patent
Strom et al.

(10) Patent No.: US 9,737,267 B2
(45) Date of Patent: Aug. 22, 2017

(54) COMPOSITE SINGULARITY MAPPING

(71) Applicant: CARDIOINSIGHT TECHNOLOGIES, INC., Cleveland, OH (US)

(72) Inventors: Maria Strom, Moreland Hills, OH (US); Qingguo Zeng, Solon, OH (US); Remi Dubois, Paris (FR); Ping Jia, Solon, OH (US); Ryan Bokan, Lakewood, OH (US); Venkatesh Vasudevan, Beachwood, OH (US); Charulatha Ramanathan, Solon, OH (US); Brian P. George, Medina, OH (US)

(73) Assignee: Cardioinsight Technologies, Inc., Cleveland, OH (US)

( * ) Notice: Subject to any disclaimer, the term of this patent is extended or adjusted under 35 U.S.C. 154(b) by 189 days.

(21) Appl. No.: 14/156,951

(22) Filed: Jan. 16, 2014

(65) Prior Publication Data
US 2014/0200467 A1 Jul. 17, 2014

Related U.S. Application Data

(60) Provisional application No. 61/753,742, filed on Jan. 17, 2013.

(51) Int. Cl.
*A61B 5/00* (2006.01)
*A61B 5/0402* (2006.01)
(Continued)

(52) U.S. Cl.
CPC .......... *A61B 5/7282* (2013.01); *A61B 5/0044* (2013.01); *A61B 5/0402* (2013.01);
(Continued)

(58) Field of Classification Search
CPC ... A61B 5/7282; A61B 5/0035; A61B 5/0205; A61B 5/7425
See application file for complete search history.

(56) References Cited

U.S. PATENT DOCUMENTS

| 8,311,618 B2 | 11/2012 | Vajdic et al. |
| 2003/0078494 A1 | 4/2003 | Panescu |

(Continued)

FOREIGN PATENT DOCUMENTS

WO 2012092016 7/2012

OTHER PUBLICATIONS

Ramanathan, C., et al.; "Noninvasive Electrocardiographic Imaging or Cardiac Electrophysiology and Arrhythmia", Nature Medicine, Nature Publishing Group, New York, NY, US, vol. 10, No. 4, Apr. 1, 2004, pp. 442-428.

(Continued)

*Primary Examiner* — Joseph Dietrich
(74) *Attorney, Agent, or Firm* — Tarolli, Sundheim, Covell & Tummino LLP

(57) ABSTRACT

A method can include storing a plurality of data sets including values computed for each of a plurality of points for a given spatial region of tissue, the values in each of the data sets characterizing electrical information for each respective point of the plurality of points for a different time interval. The method can also include combining the values computed for each of a plurality of points in a first interval, corresponding to a first map, with the values for computed for each of the respective plurality of points in another interval and to normalize the combined values relative to a common scale. The method can also include generating a composite map for the given spatial region based on the combined values that are normalized.

28 Claims, 14 Drawing Sheets

(51) Int. Cl.
*A61B 5/044* (2006.01)
*A61B 5/0476* (2006.01)

(52) U.S. Cl.
CPC ............ *A61B 5/044* (2013.01); *A61B 5/7425* (2013.01); *A61B 5/0042* (2013.01); *A61B 5/0476* (2013.01)

(56) References Cited

U.S. PATENT DOCUMENTS

| | | |
|---|---|---|
| 2007/0299352 A1 | 12/2007 | Harlev |
| 2008/0188765 A1* | 8/2008 | Stolarski ............ A61B 5/04525 600/518 |
| 2011/0118616 A1* | 5/2011 | Vajdic ................. A61B 5/0452 600/509 |
| 2012/0184858 A1 | 7/2012 | Harlev |
| 2013/0006131 A1* | 1/2013 | Narayan ................ A61B 5/042 600/508 |
| 2013/0274582 A1* | 10/2013 | Afonso ................ A61B 5/0422 600/374 |

OTHER PUBLICATIONS

Supplemental European Search Report, Applicant: CardioInsight Technologies, Inc., European Application No. 14740654, Date of Completion: Jul. 29, 2016; 8 pgs.

\* cited by examiner

COMPOSITE SINGULARITY MAPPING

RELATED APPLICATION

This application claims the benefit of U.S. Provisional Patent Application No. 61/753,742 filed Jan. 17, 2013 and entitled COMPOSITE SINGULARITY MAPPING, the entire contents of which is incorporated herein by reference.

TECHNICAL FIELD

This disclosure relates to signal mapping and, more particularly to composite singularity mapping of physiological signals.

BACKGROUND

Electrocardiographic mapping (ECM) is a technology that is used to determine and display heart electrical information from sensed electrical signals. Mapping of cardiac electrical activity becomes further complicated in the presence of certain types of arrhythmia such as fibrillation, including atrial and ventricular fibrillation.

SUMMARY

This disclosure relates to signal mapping and, more particularly to composite singularity mapping of physiological signals.

In one example, a method can include storing a plurality of data sets including values computed for each of a plurality of points for a given spatial region of tissue, the values in each of the data sets characterizing electrical information for each respective point of the plurality of points for a different time interval. The method can also include combining the values computed for each of a plurality of points in a first interval, corresponding to a first map, with the values for computed for each of the respective plurality of points in another interval and to normalize the combined values relative to a common scale. The method can also include generating a composite map for the given spatial region based on the combined values that are normalized.

In another example, a computer-implemented method can include aggregating a value computed for each of a plurality of points of a geometric surface in a first interval of a plurality of intervals, corresponding to a first map, with a value computed for each respective point of the plurality of points of the geometric surface in at least a second interval of the plurality of intervals, corresponding to a second map, to provide a composite map. The values for each of the plurality of points of the geometric surface in the composite map can be normalized to a common scale. The aggregating and the normalizing can be repeated to generate at least another composite map based on the first map, the second map and at least one other map that includes a respective value computed for each respective point of the plurality of points of the geometric surface until convergence criteria is satisfied for a plurality of successively generated composite maps for the geometric surface.

DETAILED DESCRIPTION

Figure 1:
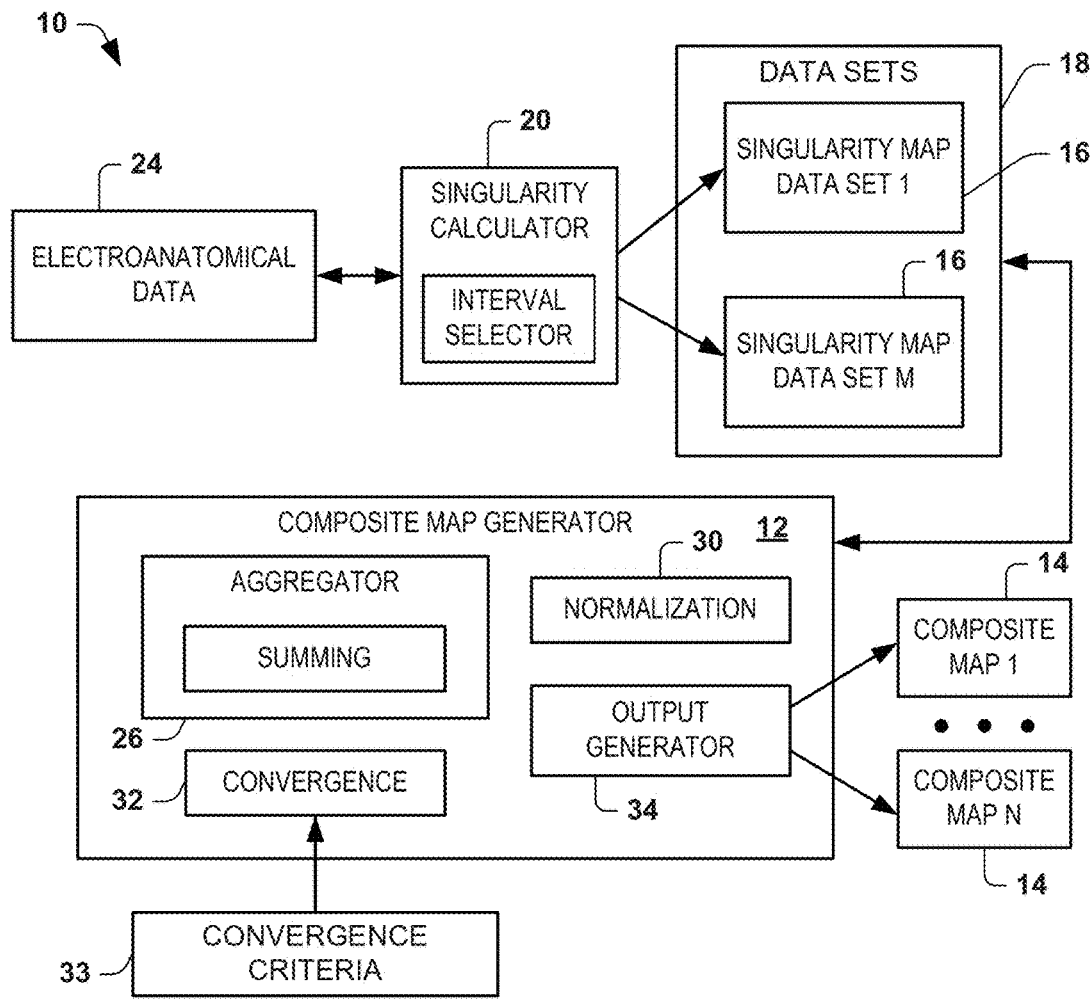
FIG. 1 depicts an example of a system for composite mapping of singularities.

This disclosure relates to signal mapping and, more particularly to composite singularity mapping of physiological signals. The composite singularity mapping can be utilized to identify and visualize a spatial singularity that can vary over time, such as a singularity of electrical activity on an anatomical structure, such as muscle tissue (e.g., the heart) or the brain. The singularity can be a phase singularity (e.g., points of detected fibrillation or tachycardia), a focal trigger or other singularity that can be mapped consistently onto a spatial region, such as a geometrical surface associated with an anatomical structure (e.g., the heart or brain).

For the example of a phase singularity, a phase value for each of a plurality of points for a given region of the muscle tissue can be computed for multiple time intervals. A phase map can be generated for the given region for one of the multiple intervals. The phase computed for each of the plurality of points of the given region for the one of the intervals can be aggregated with the phase computed for each of the respective points of the same given region for another of the intervals to provide a composite map for the region that includes aggregate phase values computed from different intervals. This aggregation of phase values for points residing in a given spatial region can be performed with respect to any number of time intervals. The region can range from a single point (e.g., represented by a pixel or voxel), one or more non-contiguous regions in two or three-dimensions, to the entire anatomical structure in three-dimensional space. For example, the region can correspond to a surface of the heart, such as can be an epicardial surface region or an endocardial surface region or a combination thereof.

The phase maps for the given region, including one of the intervals and one or more aggregate intervals can be visualized graphically in an animated sequence of maps. Each of the maps in the sequence can include a different amount of aggregation, such as by increasing the amount of aggregation of electrical phase information from more intervals in a subsequent map as compared to a preceding map. Thus, each subsequent map can represent a greater level of aggregate phase information.

As a further example, computed phase values for a first interval can be presented in a first graphical map and displayed to the user. A second graphical map, corresponding to a first composite map, can include phase values from the first interval and another (e.g., a second) interval. The phase values for each of the points in the composite map can be computed by summing the phase from each of the intervals being aggregated and by normalizing the summed values to a common scale. A third graphical map, corresponding to a second composite map, can include phase values from the first and second intervals and yet another interval. The phase values for each of the points in the third composite map can be computed by summing the phase from each of the intervals being aggregated (e.g., the first second and third intervals) and by normalizing the summed phase value for each respective point to a common scale. This process can be repeated for any number of intervals for which phase values have been computed. The resulting graphical maps can be displayed in sequence in which each subsequent map is a composite map generated from a greater number of intervals than a previous map.

The mapping technology can be used as part of a diagnostic and/or treatment workflow to facilitate the identification and location of arrhythmia mechanisms (e.g., fibrillation, tachycardia, bradycardia etc.) based on electrical activity acquired for the patient. In some examples, the electrical activity acquired for the patient can include non-invasive body surface measurements of body surface electrical activity. Additionally or alternatively, the electrical activity acquired for the patient can include invasive measurements of heart electrical activity, including epicardial measurements and/or endocardial measurements.

The approach disclosed herein can also be utilized in real time or it can be implemented in relation to stored electrical data previously acquired for a given patient. The resulting phase data can also be utilized to generate a graphical visualization to present spatially and temporally consistent information from the one or more maps. The mapping outputs can be further graphically represented as 3D maps including dynamic animated movies depicting convergence of singularities across a geometric surface, such as a surface of the heart (e.g., epicardial and/or endocardial). The spatial location of a given singularity can be used to define one or more clinical targets for performing a therapy, such as disclosed herein (see, e.g., FIG. 4).

FIG. 1 depicts an example of a system 10 to implement composite mapping. The system 10 includes a composite map generator 12 that is programmed to generate one or more composite maps 14, demonstrated as composite map 1 through composite map N, where N is a positive integer denoting the number of composite maps. In the example of FIG. 1, the composite map generator 12 generates the composite maps 14 based on a plurality singularity map data sets 16, demonstrate as data sets 1 through M, where M is a positive integer indicating the number of respective data sets 18. In some examples, the number M of data sets can be greater than or equal to number N of composite maps.

The singularity data sets 16 can collectively define a collection of data sets 18 available to the composite map generator 12. The plurality of data sets 16 can include values computed for each of a plurality of points for a given spatial region of tissue such as can be used to provide respective singularity maps according to electrical data utilized to compute the values. For instance, the values in each of the data sets 16 can be derived from electrical information for each of the plurality of points on a geometric surface (e.g., a spatial region of the heart) for a different time interval.

As an example, a singularity calculator 20 can compute a value characterizing a cardiac singularity for each of a plurality of points in the given spatial region of the heart. Examples of singularities that can be computed by the singularity calculator 20 for each of the points on the spatial region can include a phase singularity, a focal trigger and the like. The singularity calculator 20 can compute such values to represent an indexed value according to a predefined scale, for example. In some cases, each value can represent a likelihood or probability of the existence of a singularity at each respective point on the surface. The singularity calculator 20 can be programmed to compute one or more singularities for each point on the spatial region of the heart based on electroanatomical data (e.g., data describing electrical information in relation to anatomical structures) of tissue of the patient (e.g., human or other animal). As disclosed herein, the anatomical structures of the heart can be represented as a geometric surface or a surface model, such as can represent an epicardial or an endocardial surface. The geometry can be patient specific (e.g., based on imaging data for the patient) or it can be a generic model or it can be a custom model that is generated based on patient-specific data (e.g., imaging data, patient measurements and/or the like).

The singularity values computed for each of the points in the given spatial region(s) for a respective time interval can provide a singularity map, as represented by each singularity map data set 16. The singularity calculator 20 can employ an interval selector 22 to select an interval for computing each singularity map data set 16. The interval can be a contiguous interval of time or it can be a concatenation or otherwise derived from non-contiguous intervals. The interval selector 22 can select the interval automatically or in response to a user input selecting one or more time intervals. The singularity calculator 20 can compute a characteristic for each of the points of the given spatial region on the electroanatomical data for a patient as selected by the interval selector 22. There can be any number M of singularity maps (represented by the singularity data sets 16) according to the number of intervals selected.

The composite map generator 12 can include an aggregator programmed to generate one or more composite maps by combining values for each respective point among more than one singularity maps. The aggregator 26, for example, can employ a summing function 28 to sum the values each respective point from multiple time intervals, such as by summing cardiac singularity values for each point of two different maps for the same region. The composite map generator 12 can also include a normalization function 30 to normalize the summation values for each point in the resulting composite map to a common scale. For example, the normalization function 30 can be programmed to normalize each composite map relative to a scale utilized in the first singularity map that is utilized in generating the composite map. By normalizing each of the composite maps to the same scale, a graphical representation of each of the composite maps and an initial map provided in a given color or gray scale can be easily compared to each other visually. The common scale further facilitates correlation and comparison between respective values for the same points in different maps.

Any number N of the composite maps can be generated. To facilitate identifying stable singularities in the maps, the composite map generator can be programmed to compute a number N of the maps until convergence occurs between successive composite maps for the given spatial region. For example, the composite map generator can be programmed to implement a convergence function 32 to perform a correlation between computed phase values for the plurality of points of one composite map relative to each of the same plurality of points of a next successive composite map. The correlation can be a point to point comparison (e.g., by subtraction) of singularity data values for each of the respective points (e.g., nodes) in consecutively generated composite maps. Other approaches can be utilized to perform the correlation. As disclosed herein, each successive composite map is generated from one or more other maps, which can include one or more preceding composite maps. Thus, the singularities stabilize with increasing confidence as more composite maps are generated. The convergence function 32 can determine that the singularity has stabilized if convergence criteria (e.g., a threshold data) 33 has been satisfied. For example, the convergence function 32 can be programmed to compare the correlation values relative to a threshold to determine the convergence for each singularity (e.g., point or region). The threshold can be predefined or it can be programmable, such as in response to a user input. In other examples, a time-based criteria or a specified number of intervals can be utilized as convergence criteria 33.

An output generator 34 can be programmed to generate a composite map for the given spatial region based on the normalized combined values. For example, the output generator 34 can be programmed to generate a graphical map for each composite map and the initial map (e.g., corresponding to a selected one of the singularity data sets 16). The graphical maps further can be visualized according to a given scale (e.g., color scale or grayscale). As a further example, the map output generator 34 can be programmed to present the composite maps 14 in a successive order to demonstrate visually convergence of each singularity in the given spatial region. The successive order can be based on utilizing an increasing number of map data sets with each subsequent map being generated and combined (directly or indirectly) to provide a given composite map. The visual presentation of convergence can be repeatedly displayed to the user in an animated loop, for example. Moreover, since the convergence can be determined automatically, a user does need to make a determination manually of when convergence occurs. However, by adjusting the convergence criteria, a user can control the number of composite maps that may be provided in a resulting animation that is generated to demonstrate singularity convergence.

Figure 2A:
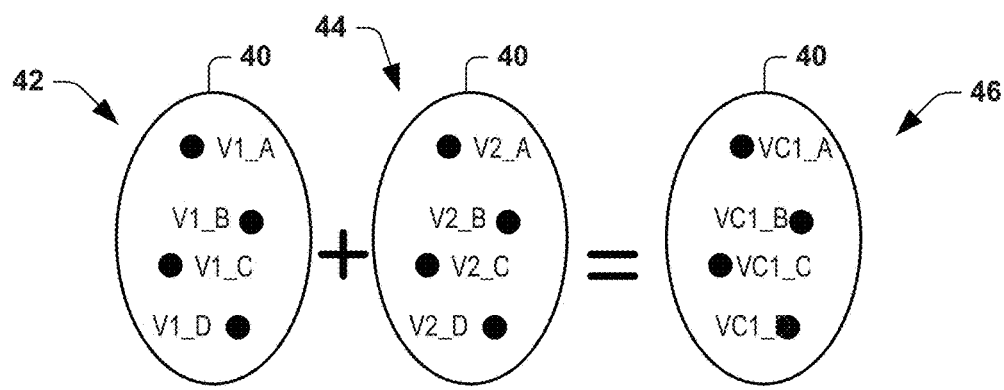
FIGS. 2A and 2B depict schematic examples of an approach that can be utilized to perform composite mapping.
Figure 2B:
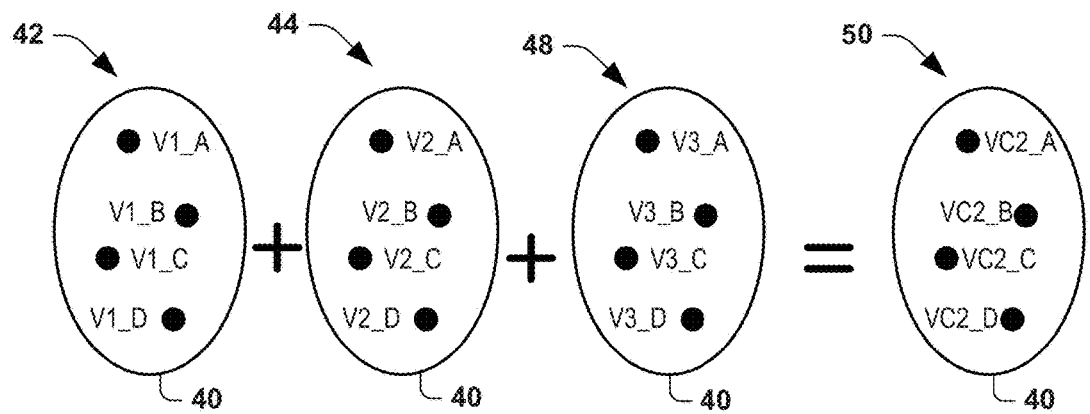

FIGS. 2A and 2B demonstrate simplified examples of an approach that can be implemented (e.g., by the composite map generator 12 of FIG. 1) to generate composite maps. In these examples, a plurality of spatial nodes A, B, C, and D are distributed across a geometric surface, demonstrated at 40. The nodes A, B, C, and D are the same respective points in the surface for each of a plurality of composite maps 42, 44 and 46. As disclosed herein, there can be any number of points and the geometric surface can have any shape in two or three dimensions. For example, the geometric surface can correspond to a surface of the heart, such as an epicardial or endocardial surface. The nodes A, B, C, and D thus can correspond to epicardial or endocardial points in each of the singularity maps (e.g., based on map data 16 of FIGS. 1) 42, 44 and 46. For instance, the number of points can include hundreds or even thousands of points for each respective map, such as may depend on the technology utilized to acquire electrical information for the surface region.

The composite map 46 can be generated by summing values for each of the respective nodes A, B, C, and D provided in the maps 42 and 44. In this example, at least the map 46 is a composite map and the maps 42 and 44 can correspond to singularity maps, each computed for a selected interval as mentioned above. Thus, the values of the nodes A, B, C and D in the composite map 46, demonstrated as VC1_A, VC1_B, VC1_C and VC1_D, can be calculated by summing the values at each respective point as follows:

$$V1\_A + V2\_A = VC1\_A$$

$$V1\_B + V2\_B = VC1\_B$$

$$V1\_C + V2\_C = VC1\_C$$

$$V1\_D + V2\_D = VC1\_D$$

The resulting singularity nodes values VC1_A, VC1_B, VC1_C and VC1_D further can be normalized to itself (map 46).

In FIG. 2B, to calculate the next successive composite map 50, each of the respective points in the singularity maps 42, 44, and 48 are summed. The map 48 can correspond to a singularity map data set (e.g., one of the map data sets 16 of FIG. 1) that has been computed from electroanatomical data for a selected interval as mentioned above. Thus V1_A, V2_A, and V3_A are summed to form VC2_A, and so forth for each of the other plurality of points. The successive composite map 50 can then be normalized to itself in order to have a common scale. To facilitate animated mapping of consecutive composite maps, each of the composite maps can be normalized to common color scale.

Thus, the values of the nodes A, B, C and D in the successive composite map 50, demonstrated as VC2_A, VC2_B, VC2_C and VC2_D, can be calculated by summing the values at each respective point as follows:

$$V1\_A + V2\_A + V3\_A = VC2\_A$$

$$V1\_B + V2\_B + V3\_B = VC2\_B$$

$$V1\_C + V2\_C + V3\_C = VC2\_C$$

$$V1\_D + V2\_D + V3\_D = VC2\_D$$

As disclosed herein, the process can be repeated to derive any number of composite maps. For instance, the computed values for each node in the composite map can be normalized after computation, and non-normalized values can combined with other values from a next singularity map, etc.

Figure 3:
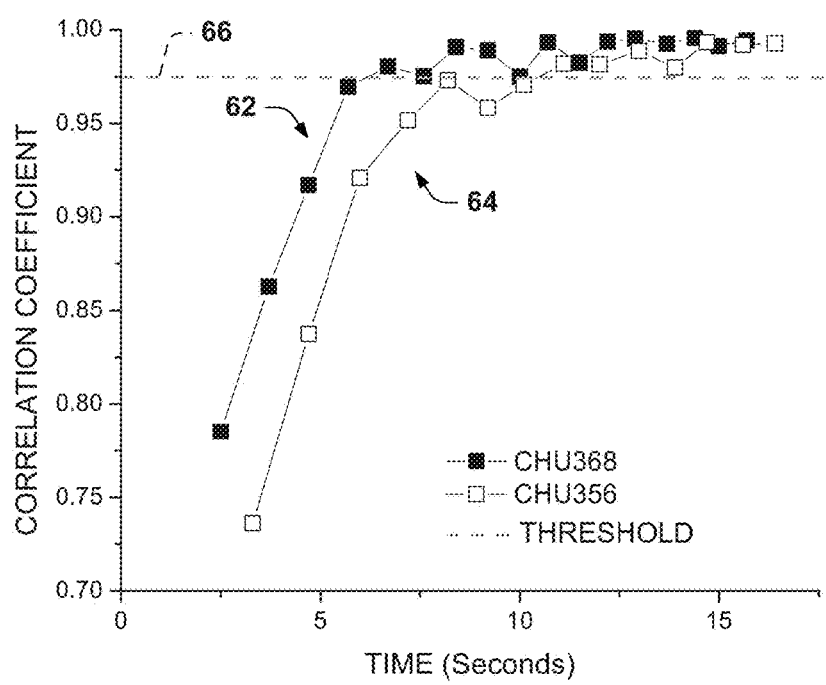
FIG. 3 is a graph of correlation coefficients plotted as a function of time for an example composite mapping process.

FIG. 3 depicts a graph of plots 62 and 64 demonstrating correlation coefficients as a function of time for different patients (e.g., patient CHU368 and patient CHU356). Within patient, CHU368, for example, 18 intervals encompassing 15.7 seconds of AF were analyzed. In the graph, each point along the respective plots represents a correlation coefficient computed between the current composite map and the previous composite map. For example, correlation value 1 was determined by the correlation coefficient computed based on composite map 1 and composite map 2. Thus, to determine convergence for composite map generation, each correlation coefficient can be compared to the correlation coefficient in a preceding composite interval.

A threshold (or other convergence criteria) 66 can be set for determining when convergence occurs. As an example, the threshold 66 can be set by a user (e.g., physician) in response to a user input. In some examples, the threshold 66 can be set to a default predetermined threshold based on an analyzing empirical evidence for a plurality of patients. In yet other examples, the threshold 66 can be set based on +/−expected variation of convergence.

Figure 4:
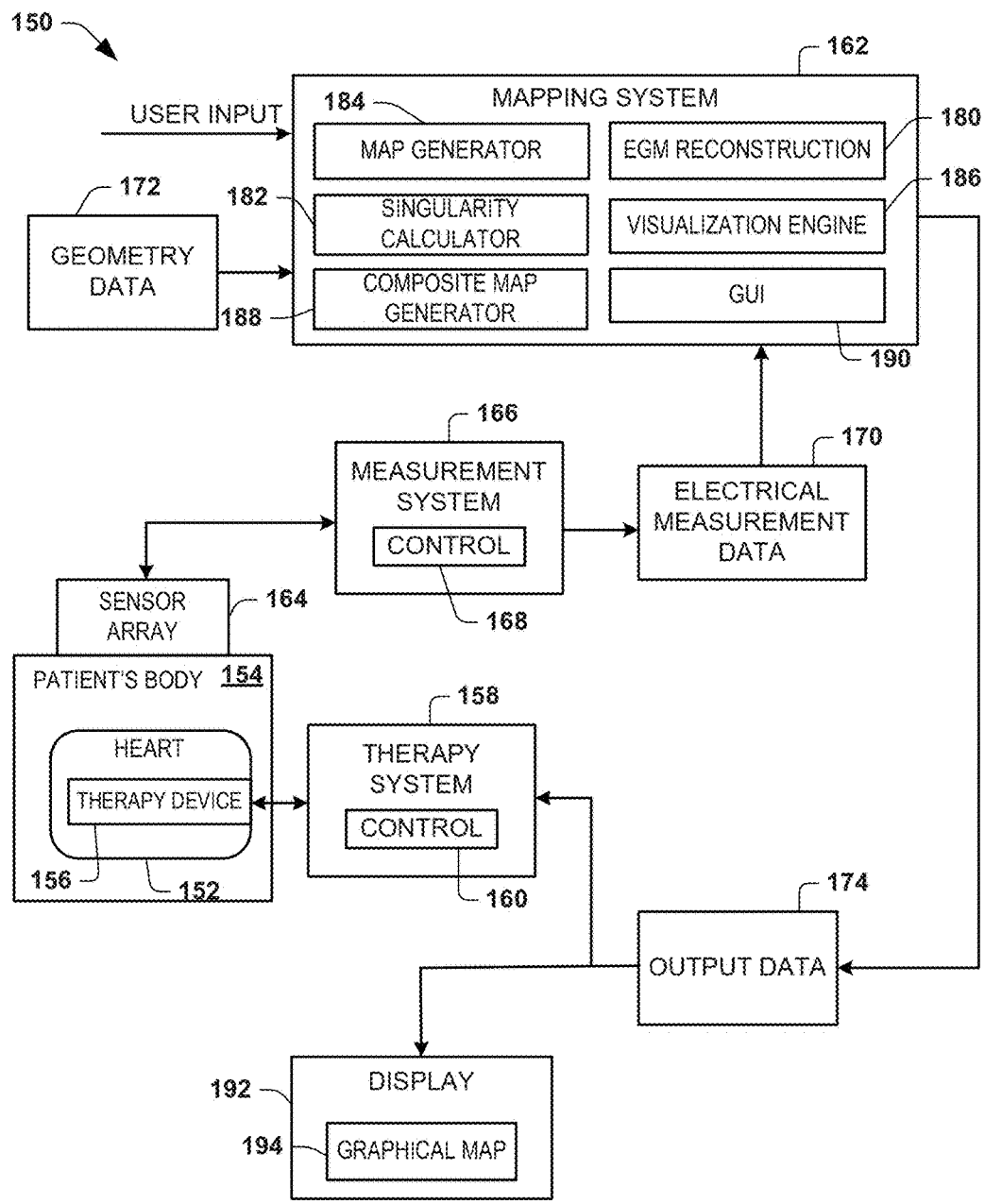
FIG. 4 depicts an example of a system that can be implemented for diagnosis and therapy delivery.
Figure 5A:
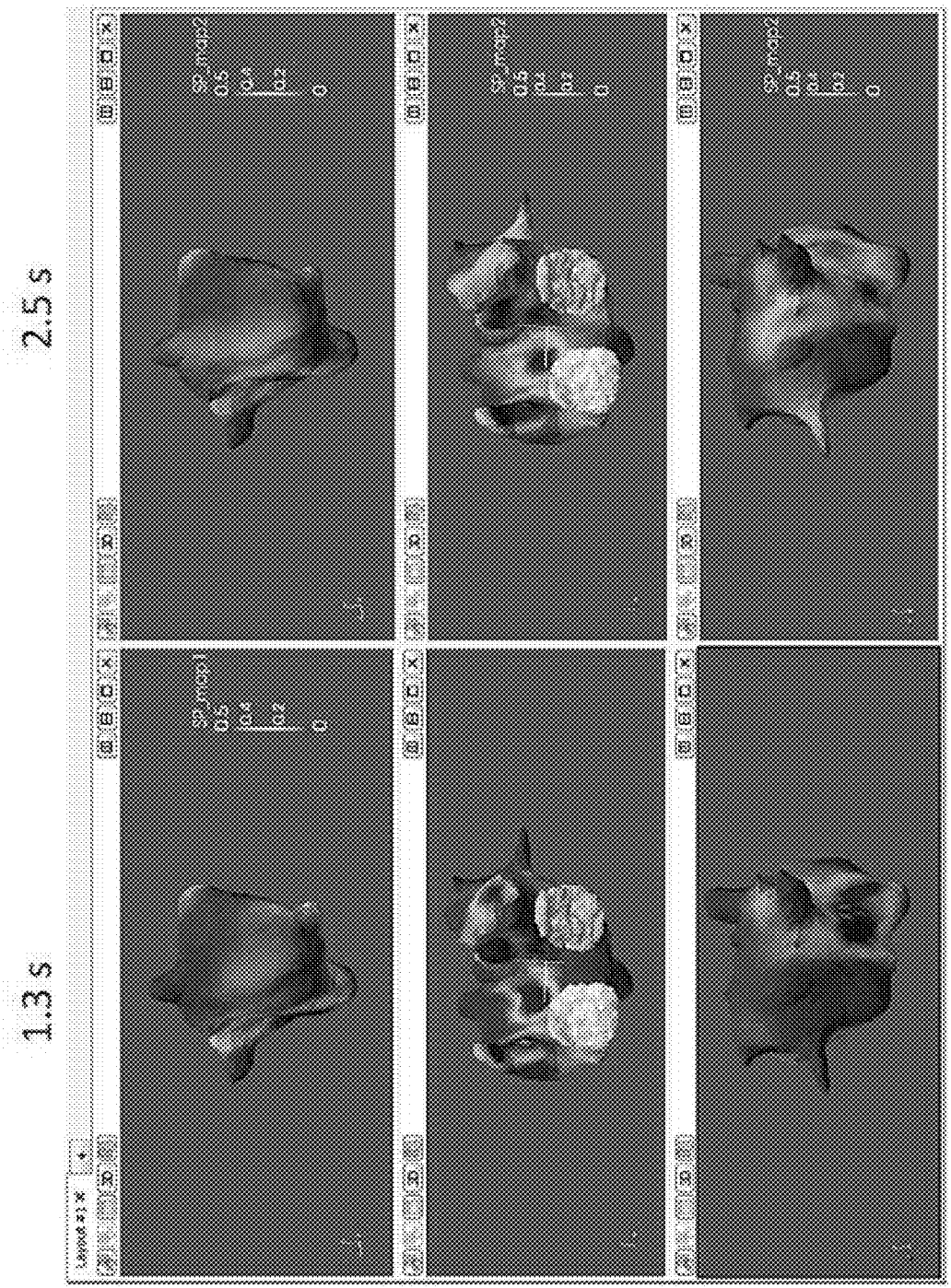
FIGS. 5A through 5I depict examples of composite maps that can be generated for heart for demonstrating convergence of phase singularities.
Figure 5B:
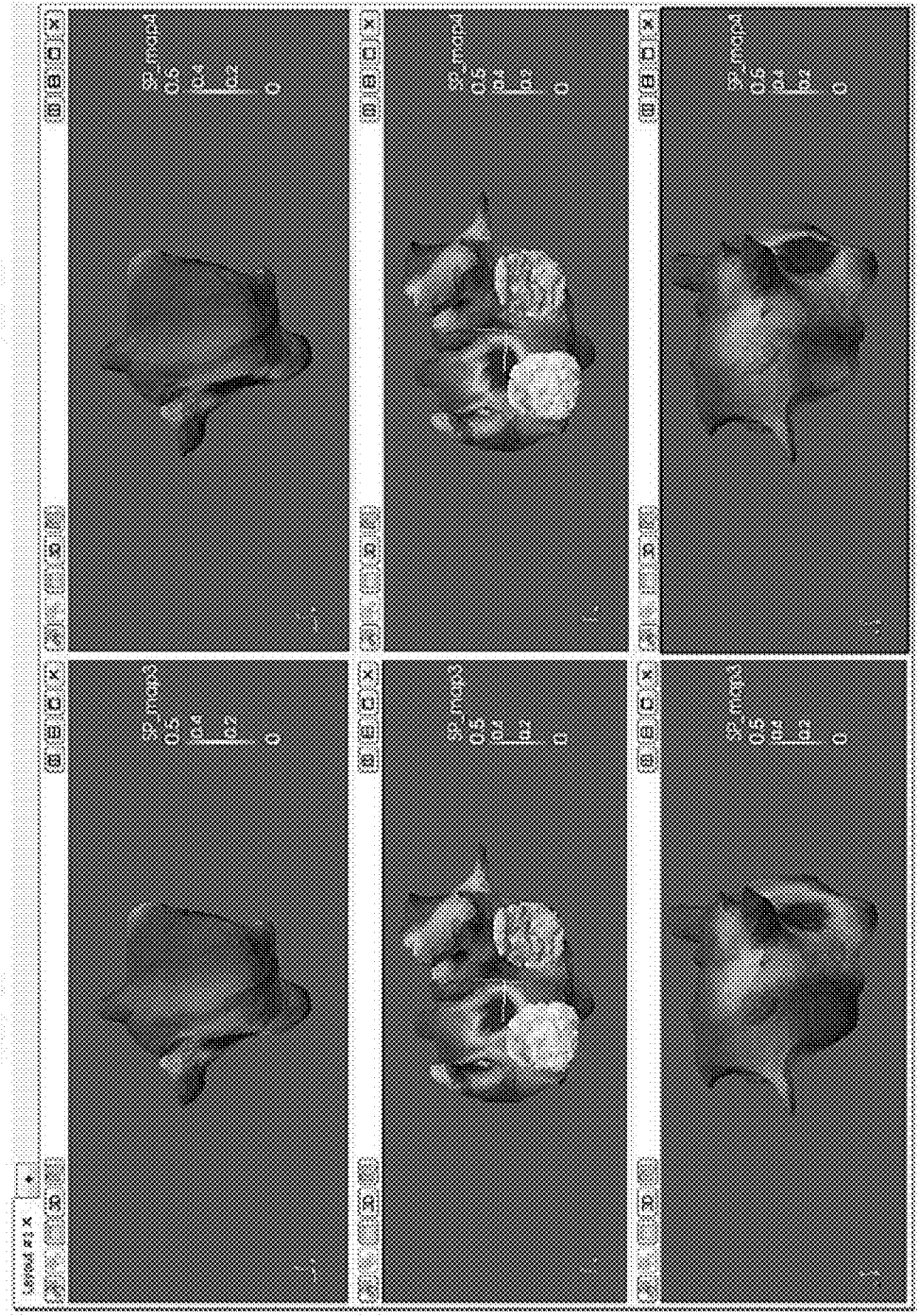
Figure 5C:
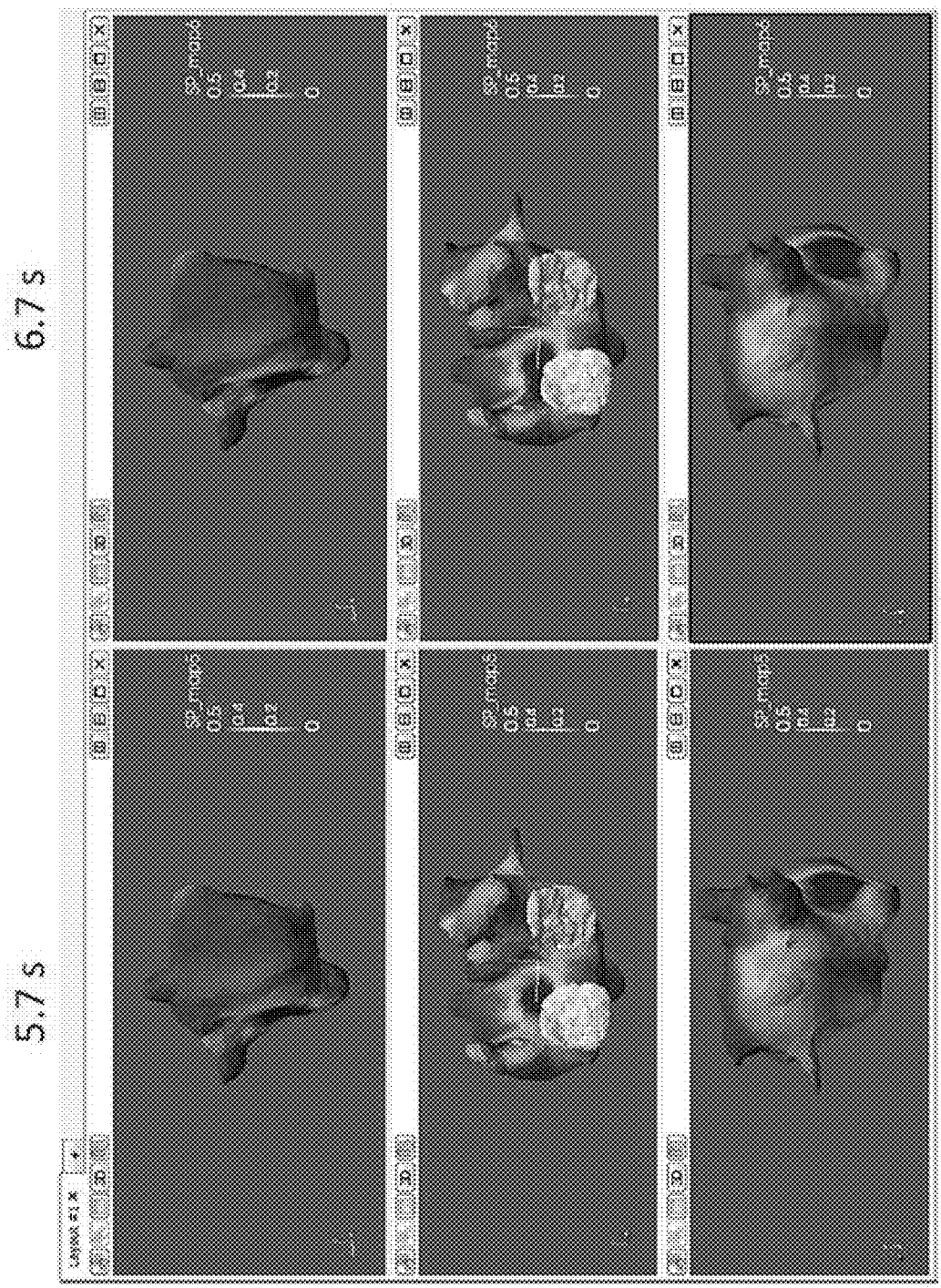
Figure 5D:
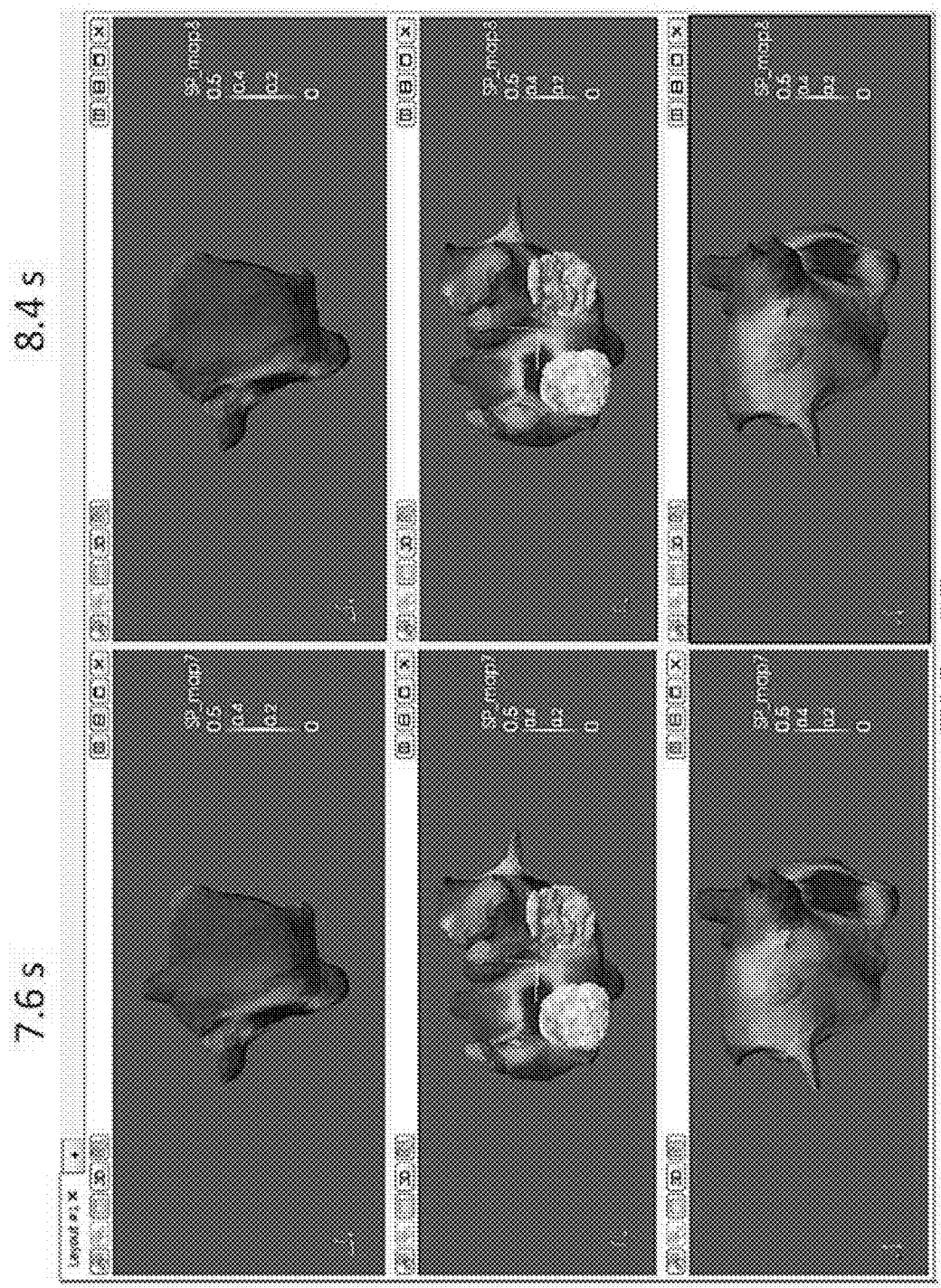
Figure 5E:
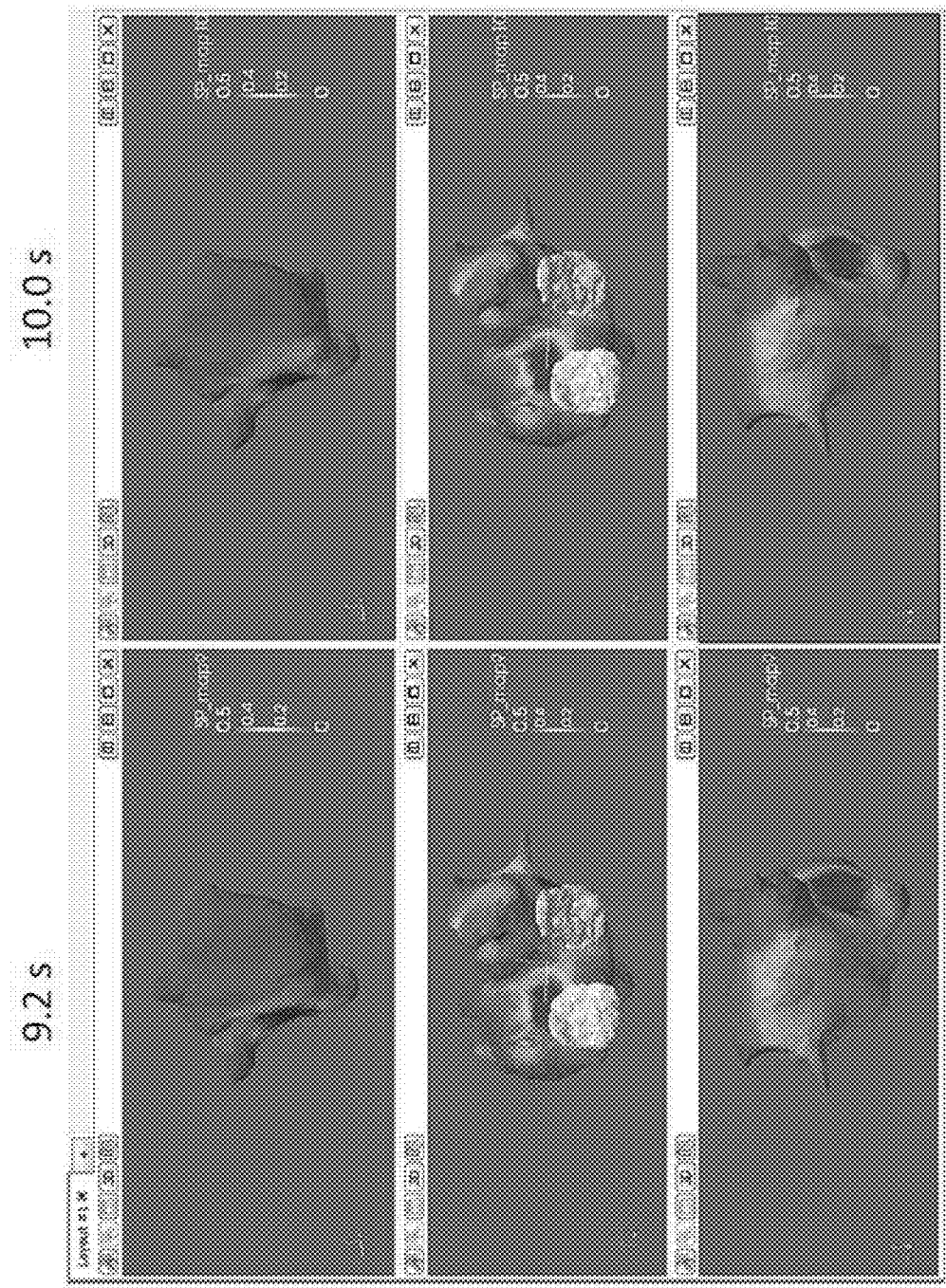
Figure 5F:
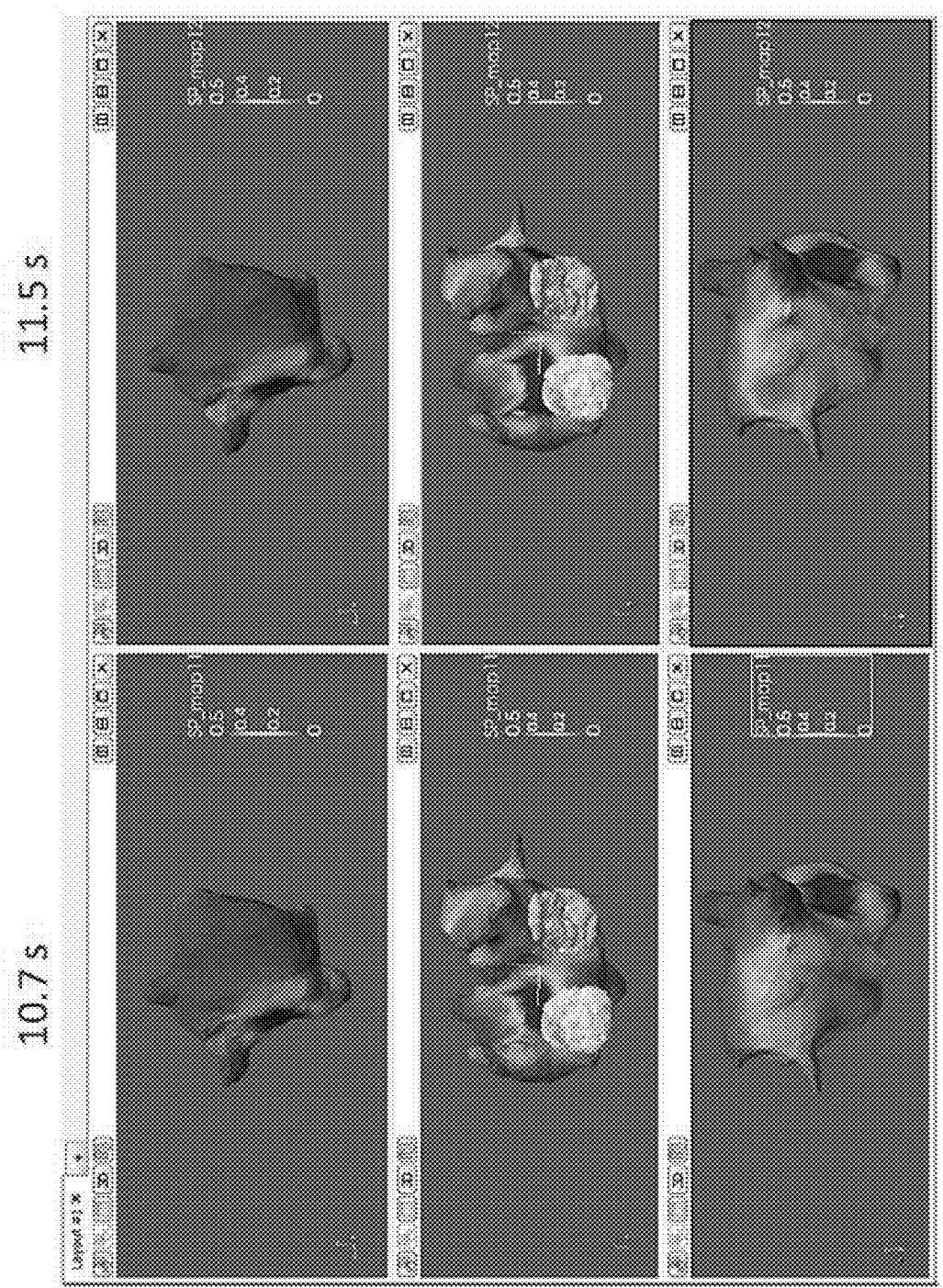
Figure 5G:
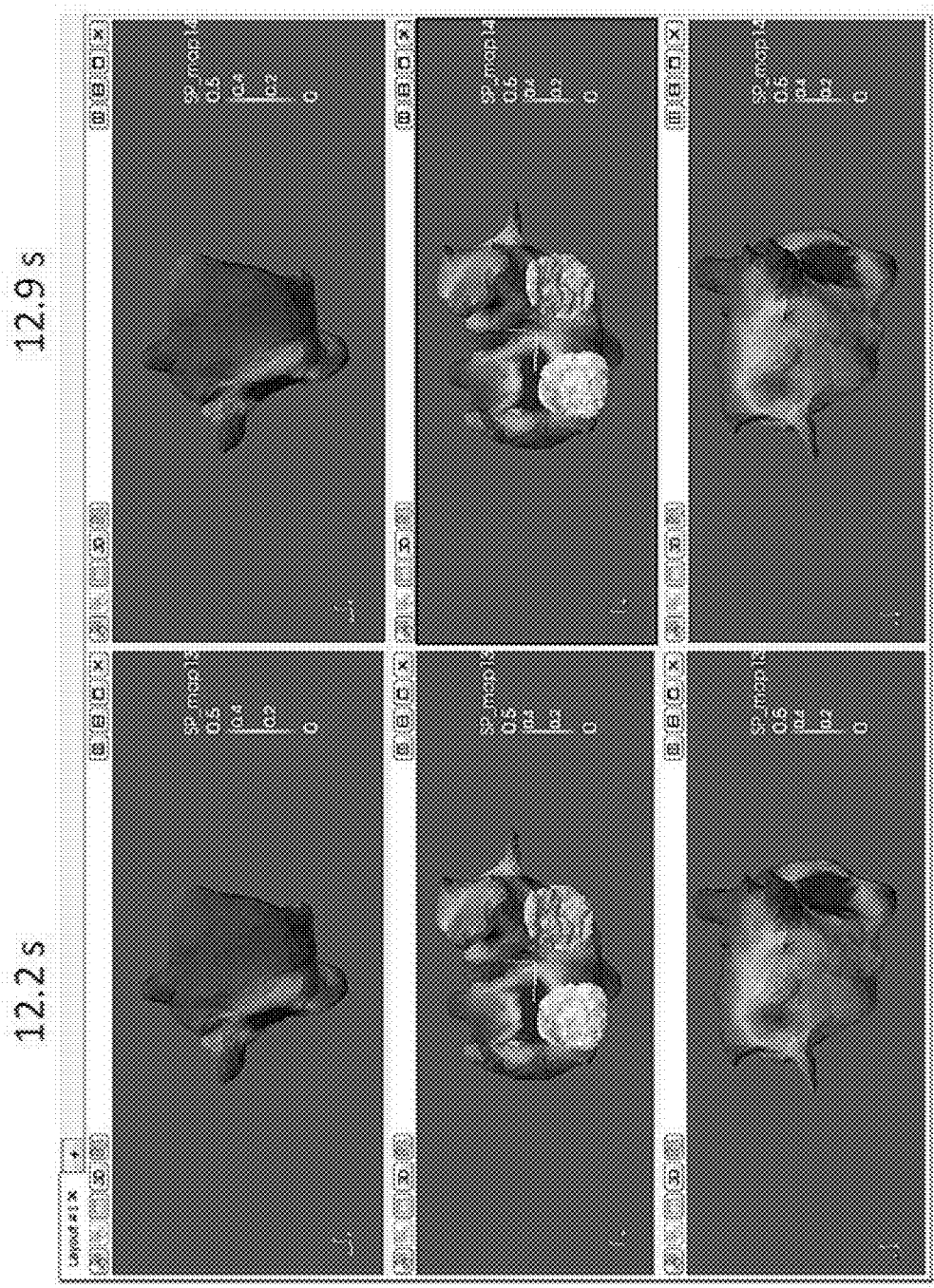
Figure 5H:
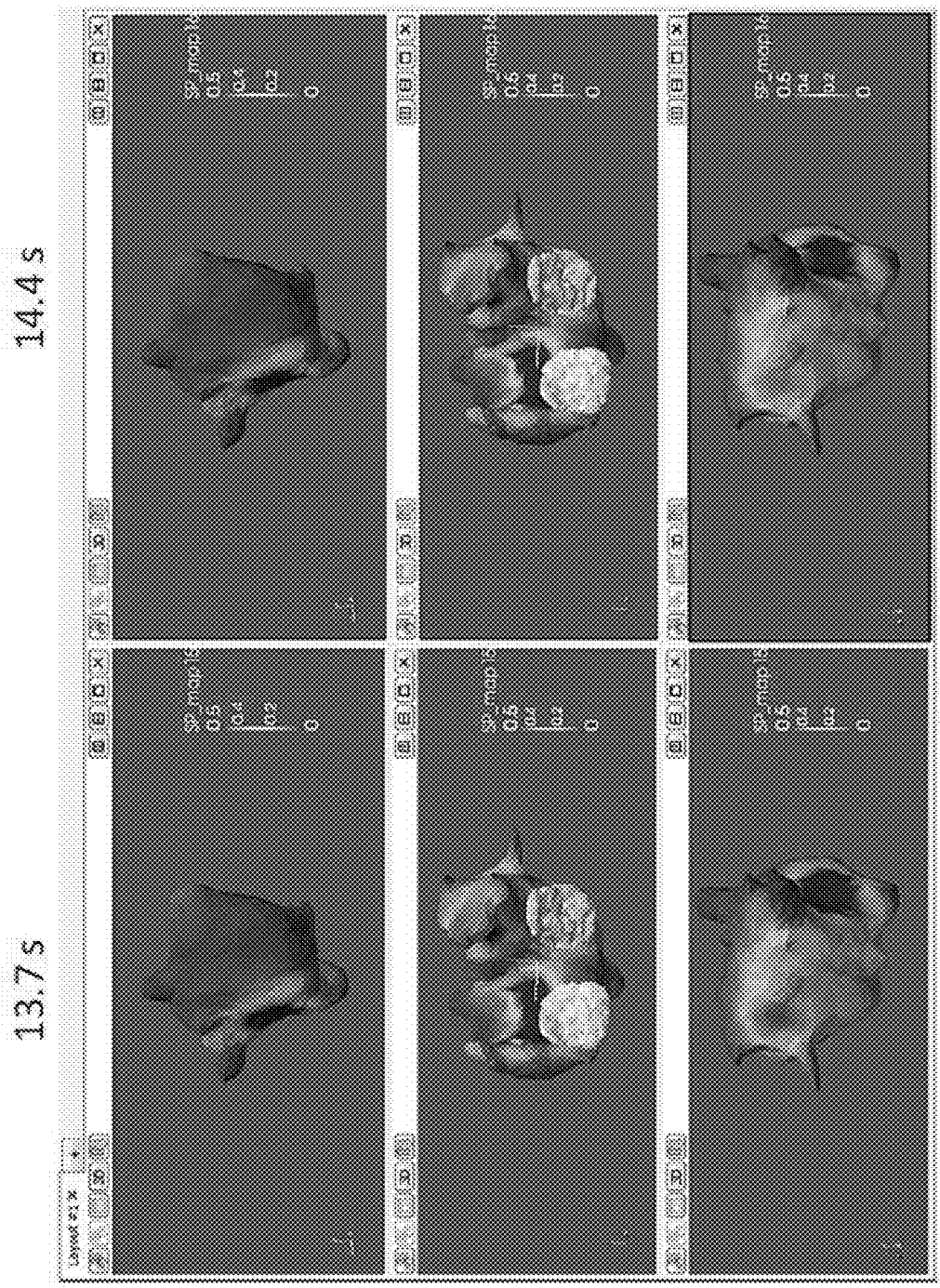
Figure 5I:
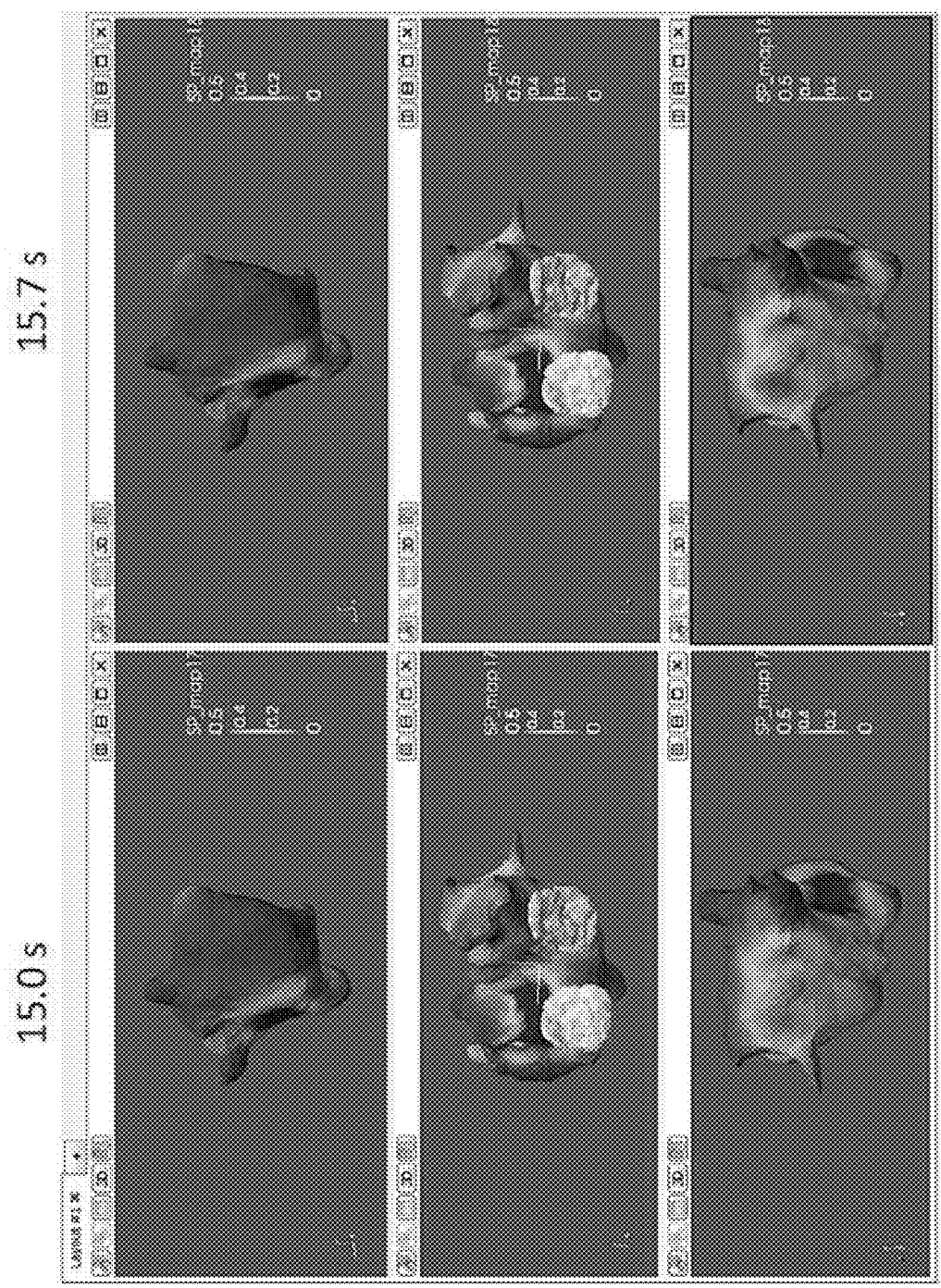

FIG. 4 depicts an example of a system 150 that can be utilized for performing diagnostics and/or treatment of a patient. In some examples, the system 150 can generate composite singularity maps for the heart 152 in real time as part of a diagnostic procedure (e.g., an electrophysiology study) to help assess the electrical activity and conduction pathways of a patient's heart.

Additionally or alternatively, the system 150 can be utilized as part of a treatment procedure, such as to help a physician determine parameters for delivering a therapy to the patient (e.g., delivery location, amount and type of therapy). For example, a catheter, such as a pacing catheter, having one or more therapy delivery devices 156 affixed thereto can be inserted into the body 154 as to contact the patient's heart 152, endocardially or epicardially. Those skilled in the art will understand and appreciate various type and configurations of therapy delivery devices 156 that can be utilized, which can vary depending on the type of treatment and the procedure. For instance, the therapy device 156 can be configured to deliver electrical therapy, chemical therapy, sound wave therapy, thermal therapy or any combination thereof.

By way of example, the therapy delivery device 156 can include one or more electrodes located at a tip of an ablation catheter configured to generate heat for ablating tissue in response to electrical signals (e.g., radiofrequency energy) supplied by a therapy system 158. In other examples, the therapy delivery device 156 can be configured to deliver cooling to perform ablation (e.g., cryogenic ablation), to deliver chemicals (e.g., drugs), ultrasound ablation, high-frequency ablation, or a combination of these or other therapy mechanisms. In still other examples, the therapy delivery device 156 can include one or more electrodes located at a tip of a pacing catheter to deliver electrical stimulation, such as for pacing the heart, in response to electrical signals (e.g., pacing pulses) supplied by a therapy system 158. Other types of therapy can also be delivered via the therapy system 158 and the invasive therapy delivery device 156 that is positioned within the body.

As a further example, the therapy system 158 can be located external to the patient's body 154 and be configured to control therapy that is being delivered by the device 156. For instance, the therapy system 158 includes controls (e.g., hardware and/or software) 160 that can communicate (e.g., supply) electrical signals via a conductive link electrically connected between the delivery device (e.g., one or more electrodes) 156 and the therapy system 158. The control system 160 can control parameters of the signals supplied to the device 156 (e.g., current, voltage, repetition rate, trigger delay, sensing trigger amplitude) for delivering therapy (e.g., ablation or stimulation) via the electrode(s) 154 to one or more location of the heart 152. The control circuitry 160 can set the therapy parameters and apply stimulation based on automatic, manual (e.g., user input) or a combination of automatic and manual (e.g., semiautomatic controls). One or more sensors (not shown) can also communicate sensor information back to the therapy system 158. The position of the device 156 relative to the heart 152 can be determined and tracked intraoperatively via an imaging modality (e.g., fluoroscopy, xray), a mapping system 162, direct vision or the like. The location of the device 156 and the therapy parameters thus can be combined to determine corresponding therapy parameter data.

Before, during and/or after providing a therapy via the therapy system 158, another system or subsystem can be utilized to acquire electrophysiology information for the patient. In the example of FIG. 4, a sensor array 164 includes one or more electrodes that can be utilized for recording patient electrical activity. As one example, the sensor array 164 can correspond to a high-density arrangement of body surface sensors (e.g., greater than approximately 200 electrodes) that are distributed over a portion of the patient's torso for measuring electrical activity associated with the patient's heart (e.g., as part of an electrocardiographic mapping procedure). An example of a non-invasive sensor array that can be used is shown and described in International application No. PCT/US2009/063803, filed 10 Nov. 2009, which is incorporated herein by reference. Other arrangements and numbers of sensing electrodes can be used as the sensor array 164. For example, the array can be a reduced set of electrodes, which does not cover the patient's entire torso and is designed for measuring electrical activity for a particular purpose (e.g., an array of electrodes specially designed for analyzing AF and/or VF) and/or for monitoring a predetermined spatial region of the heart.

One or more sensors may also be located on the device 156 that is inserted into the patient's body. Such sensors can be utilized separately or in conjunction with the sensor array 164 for mapping electrical activity for an endocardial surface, such as the wall of a heart chamber, as well as for an epicardial surface. Additionally, such electrode can also be utilized to help localize the device 156 within the heart 152, which can be registered into an image or map that is generated by the system 150. Alternatively, such localization can be implemented in the absence of emitting a signal from an electrode within or on the heart 152.

In each of such example approaches for acquiring patient electrical information, including invasively, non-invasively, or a combination of invasive and non-invasive sensing, the sensor array(s) 164 provide the sensed electrical information to a corresponding measurement system 166. The measurement system 166 can include appropriate controls and signal processing circuitry 168 for providing corresponding measurement data 170 that describes electrical activity detected by the sensors in the sensor array 164. The measurement data 170 can include analog and/or digital information.

The control 168 can also be configured to control the data acquisition process for measuring electrical activity and providing the measurement data 170. In some examples, the control 168 can control acquisition of measurement data 170 separately from the therapy system operation, such as in response to a user input. In other examples, the measurement data 170 can be acquired concurrently with and in synchronization with delivering therapy by the therapy system, such as to detect electrical activity of the heart 152 that occurs in response to applying a given therapy (e.g., according to therapy parameters). For instance, appropriate time stamps can be utilized for indexing the temporal relationship between the respective measurement data 170 and therapy parameters use to deliver therapy as to facilitate the evaluation and analysis thereof.

The mapping system 162 is programmed to combine the measurement data 170 corresponding to electrical activity of the heart 152 with geometry data 172 by applying appropriate processing and computations to provide corresponding output data 174. The output data 174 can be represent or characterize phase across the cardiac envelope (e.g., on a surface of the heart 152).

As one example, the output data 174 can include singularity maps and resulting composite singularity maps derived from the electrical measurement data acquired for the patient over various time intervals. In some examples, the output data 174 can include one or more composite phase singularity maps based on phase data computed for a geometric surface of the patient's heart 152. As disclosed herein, the composite maps can be computed based on electrical data that is acquired non-invasively via sensors 164 distributed on the surface of the patient's body 154, acquired invasively via electrodes position on or within the heart or is acquired both invasively and non-invasively.

Since the measurement system 166 can measure electrical activity of a predetermined region or the entire heart concurrently (e.g., where the sensor array 164 covers the entire thorax of the patient's body 154), the resulting output data (e.g., phase characterizations and/or other electrocardiographic maps) thus can also represent concurrent data for the predetermined region or the entire heart in a temporally and spatially consistent manner. The time interval for which the output data/maps are computed can be selected based on user input. Additionally or alternatively, the selected intervals can be synchronized with the application of therapy by the therapy system 158.

For the example where the electrical measurement data is obtained non-invasively (e.g., via body surface sensor array 164), electrogram reconstruction 180 can be programmed to compute an inverse solution and provide corresponding reconstructed electrograms based on the process signals and the geometry data 172. The reconstructed electrograms thus can correspond to electrocardiographic activity across a cardiac envelope, and can include static (three-dimensional at a given instant in time) and/or be dynamic (e.g., four-dimensional map that varies over time). Examples of inverse algorithms that can be utilized in the system 10 include those disclosed in U.S. Pat. Nos. 7,983,743 and 6,772,004, which are incorporated herein by reference. The EGM reconstruction 180 thus can reconstruct the body surface electrical activity measured via the sensor array 164 onto a multitude of locations on a cardiac envelope (e.g., greater than 1000 locations, such as about 2000 locations or more). In other examples, the mapping system 162 can compute electrical activity over a sub-region of the heart based on electrical activity measured invasively, such as via a basket catheter or other form of measurement probe.

As disclosed herein, the cardiac envelope can correspond to a three dimensional surface geometry corresponding to a patient's heart, which surface can be epicardial or endocardial. Alternatively or additionally, the cardiac envelope can correspond to a geometric surface that resides between the epicardial surface of a patient's heart and the surface of the patient's body where the sensor array 164 has been positioned. Additionally, the geometry data 172 that is utilized by the electrogram reconstruction 180 can correspond to actual patient anatomical geometry, a preprogrammed generic model or a combination thereof (e.g., a model that is modified based on patient anatomy).

As an example, the geometry data 172 may be in the form of graphical representation of the patient's torso, such as image data acquired for the patient. Such image processing can include extraction and segmentation of anatomical features, including one or more organs and other structures, from a digital image set. Additionally, a location for each of the electrodes in the sensor array 164 can be included in the patient geometry data 172, such as by acquiring the image while the electrodes are disposed on the patient and identifying the electrode locations in a coordinate system through appropriate extraction and segmentation. Other non-imaging based techniques can also be utilized to obtain the position of the electrodes in the sensor array, such as a digitizer or manual measurements.

As mentioned above, the geometry data 172 can correspond to a mathematical model, such as can be a generic model or a model that has been constructed based on image data for the patient. Appropriate anatomical or other landmarks, including locations for the electrodes in the sensor array 164 can be identified in the geometry data 172 to facilitate registration of the electrical measurement data 170 and performing the inverse method thereon. The identification of such landmarks can be done manually (e.g., by a person via image editing software) or automatically (e.g., via image processing techniques).

By way of further example, the geometry data 172 can be acquired using nearly any imaging modality based on which a corresponding representation of the geometrical surface can be constructed, such as described herein. Such imaging may be performed concurrently with recording the electrical activity that is utilized to generate the patient measurement data 170 or the imaging can be performed separately (e.g., before or after the measurement data has been acquired).

Following (or concurrently with) determining electrical potential data (e.g., electrogram data computed from non-invasively and/or invasively acquired measurements) across the geometric surface of the heart, the electrogram data can further undergo signal processing to compute one or more cardiac maps. The mapping system 162 can include a singularity calculator 182 that can be programmed to compute a characteristic of a cardiac singularity computed for each of a plurality of points in the given spatial region based on the reconstructed electrogram data. For example, the singularity calculator can be programmed to compute phase singularity data across a given geometric surface of the patient's heart. An example of an approach that the singularity calculator 182 can implement to compute a phase singularity value for each of the plurality of points in the given spatial region and to generate corresponding phase singularity map of the heart is disclosed in PCT Application No. PCT/US13/60851 filed Sep. 20, 2013, which is incorporated herein by reference. As disclosed herein, the singularity calculator 182 can also compute other types of singularities, including focal triggers and focal trigger maps or other cardiac phenomena capable of exhibiting spatial and temporal recurrence over a plurality of time intervals.

A composite map generator 188 can be programmed to generate composite maps based on the computed cardiac singularities for a given geometric surface. For example, the composite map generator 188 can aggregate (e.g., sum) a value computed for each of a plurality of nodes distributed over a geometric surface over two or more time intervals of a plurality of such intervals. The computed values for each of the plurality of points of the geometric surface in the composite map further can be normalized to a predetermined common scale to facilitate evaluation of the prospective phase singularities. The composite map generator 188 can repeat the aggregating and the normalizing with singularity maps determined for one or more additional time intervals until convergence is detected between successively generated composite maps. Convergence can be determined based on a correlation between the plurality of points of the geometric surface for consecutively generated composite maps. For example, correlation coefficients can be computed from the consecutive composite maps and compared relative to a threshold to determine the convergence.

The output data 174 can be converted to a graphical representation for display by a visualization engine 186. Parameters associated with the graphical representation, corresponding to an output visualization, such as including selecting a time interval, a type of information that is to be presented in the visualization and the like can be selected in response to a user input via a corresponding visualization GUI 190. The mapping system 162 thus can generate corresponding output data 174 that can in turn be rendered by the visualization engine 186 as a corresponding graphical output in a display 192, such as including an electrocardiographic phase map (e.g., a composite phase singularity map) 194.

In addition to the mapping system 162 generating composite singularity maps (e.g., for phase singularities, trigger focal points or other cardiac singularities), the mapping system can also be configured to implement other types of electrocardiographic mapping such as including activation maps, dominant frequency maps and the like. For example, the display 192 can include one or more regions for displaying composite singularity map data concurrently with corresponding activation or dominant frequency maps to facilitate diagnosis and treatment of AF or VF.

Additionally, the output data 174, including information about the size and location of cardiac singularities determined from the composite singularity maps, can be provided to the therapy system 158. The control 160 of the therapy system can utilize the output data to control one or more therapy parameters. As an example, the control 160 can control delivery of ablation therapy to a site of the heart (e.g., epicardial or endocardial wall) based on the location and size of a phase singularity determined from a composite phase singularity map. Other types of therapy can also be controlled based on the output data. The control that is implemented can be fully automated control, semi-automated control (partially automated and responsive to a user input) or manual control based on the output data 174.

FIGS. 5A through 5I depict examples of composite maps that can be generated (e.g., by map generator 12 of FIG. 1) for demonstrating convergence of phase singularities. In the examples of FIGS. 5A through 5I, composite phase maps demonstrate phase information for three different surface regions of a patient's heart. Each of the FIGS. 5A through 5I represent composite phase data calculated from an initial point in time (e.g., t=0) and aggregated over a plurality of intervals ranging from 1.3 s through 15.7 s.

In this example, the intervals are not evenly spaced apart further demonstrating that the different amounts of time can be implemented between each adjacent pairs of successive intervals. For instance, predetermined electrical information (e.g., phase values) can be detected and used (e.g., by interval selector 22) to select each of the respective intervals used to generate corresponding singularity map data sets. In other examples, a predetermined fixed time interval can be utilized.

As demonstrated in the examples of FIGS. 5A through 5I, a later time value indicates a greater number of data sets being aggregated which promotes convergence of singularities being visualized in the later composite maps. As mentioned, the map generator 12 can determine convergence relative to a convergence threshold, as disclosed herein.

Figure 6:
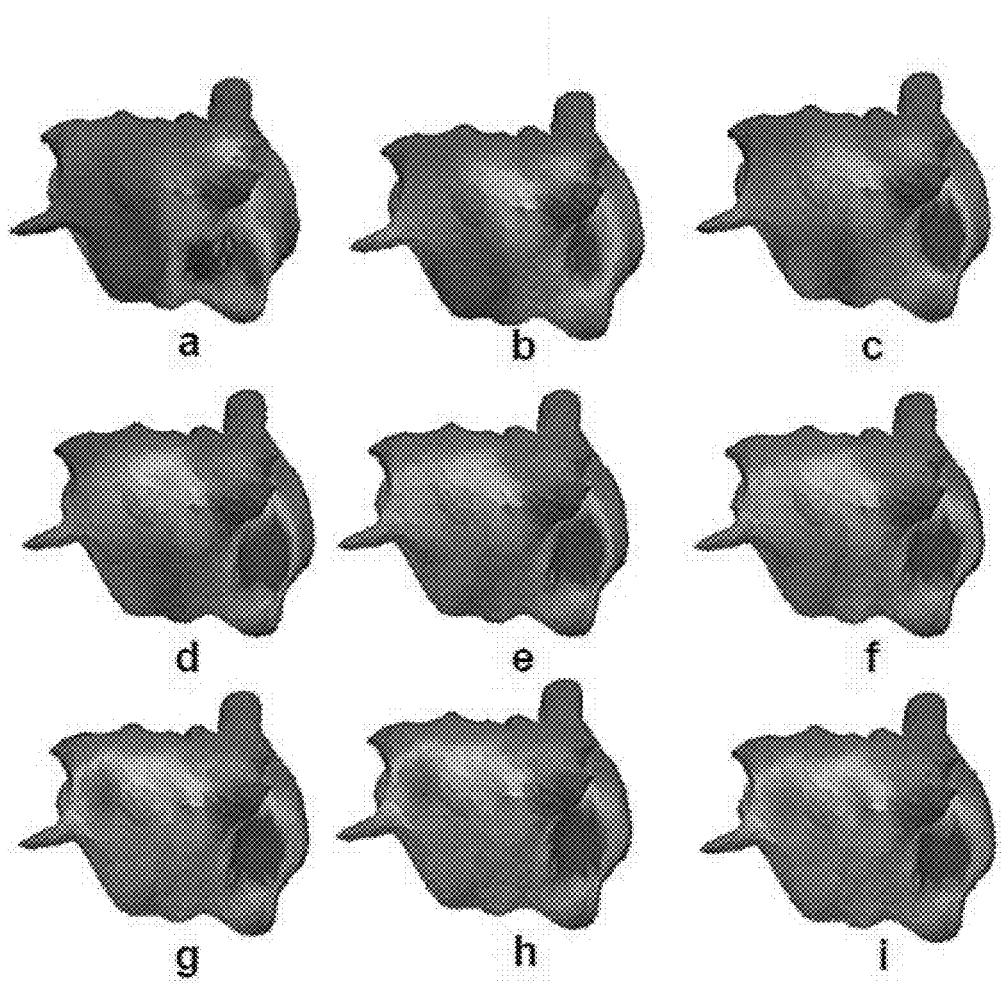
FIG. 6 depicts an example of composite phase singularity maps that can be generated to demonstrate stability of atrial fibrillation (AF).

FIG. 6 depicts an example of composite phase singularity maps that can be generated to demonstrate stability of AF foci on the surface of a patient's heart. In this example, each of the composite maps is demonstrated by respective references a, b, c, d, e, f, g, h and i. A corresponding color scale can be implemented so that the singularities can be visually differentiated in the resulting maps until a predetermined convergence occurs, such as in map "i" of FIG. 6. For instance, a blue color can be used to indicate the absence of a singularity and a red color can indicate a computed singularity, with the shade of color indicating the aggregate level of detected singularity (or absence thereof) over the set of intervals combined to produce the respective map.

Figure 7:
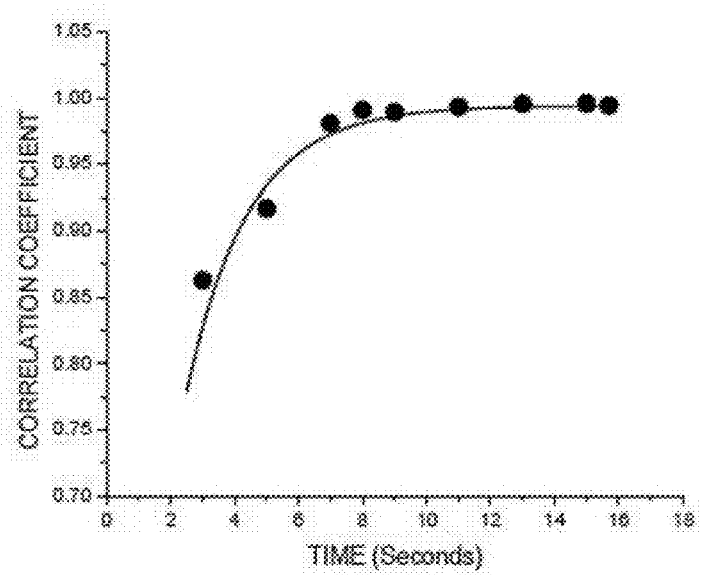
FIG. 7 is a graph of correlation coefficients plotted as a function of time for the example composite mapping of FIG. 6 to demonstrate AF stability.

FIG. 7 is a graph of correlation coefficients plotted as a function of time for the example composite mapping of FIG. 6 to demonstrate AF stability. A comparison of FIGS. 6 and 7 demonstrates that the correlation coefficient stabilizes around 7 seconds, which corresponds to composite map "c" in FIG. 6. Thus by aggregating the data sets to generate composite singularity maps, as disclosed herein, localization of cardiac singularities can be visualized effectively.

In view of the foregoing structural and functional description, those skilled in the art will appreciate that portions of the systems and method disclosed herein may be embodied as a method, data processing system, or computer program product such as a non-transitory computer readable medium. Accordingly, these portions of the approach disclosed herein may take the form of an entirely hardware embodiment, an entirely software embodiment (e.g., in a non-transitory machine readable medium), or an embodiment combining software and hardware, such as shown and described with respect to the computer system of FIG. 8. Furthermore, portions of the systems and method disclosed herein may be a computer program product on a computer-usable storage medium having computer readable program code on the medium. Any suitable computer-readable medium may be utilized including, but not limited to, static and dynamic storage devices, hard disks, optical storage devices, and magnetic storage devices.

Certain embodiments have also been described herein with reference to block illustrations of methods, systems, and computer program products. It will be understood that blocks of the illustrations, and combinations of blocks in the illustrations, can be implemented by computer-executable instructions. These computer-executable instructions may be provided to one or more processor of a general purpose computer, special purpose computer, or other programmable data processing apparatus (or a combination of devices and circuits) to produce a machine, such that the instructions, which execute via the processor, implement the functions specified in the block or blocks.

These computer-executable instructions may also be stored in computer-readable memory that can direct a computer or other programmable data processing apparatus to function in a particular manner, such that the instructions stored in the computer-readable memory result in an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks.

Figure 8:
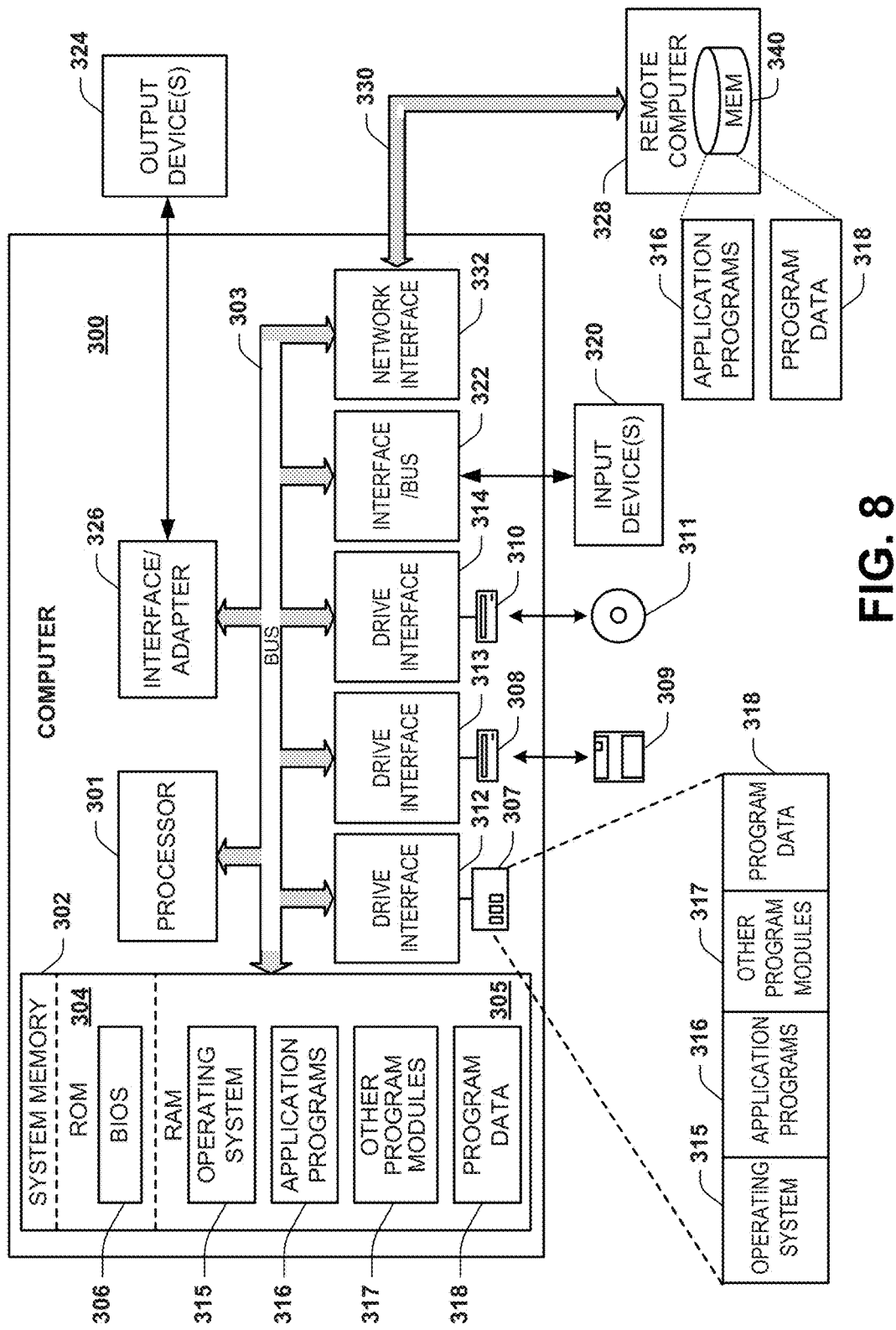
FIG. 8 depicts an example computing environment.

In this regard, FIG. 8 illustrates one example of a computer system 300 that can be employed to execute one or more embodiments, such as including acquisition and processing of sensor data, processing of image data, as well as analysis of transformed sensor data and image data associated with the analysis of cardiac electrical activity. Computer system 300 can be implemented on one or more general purpose networked computer systems, embedded computer systems, routers, switches, server devices, client devices, various intermediate devices/nodes or stand alone computer systems. Additionally, computer system 300 can be implemented on various mobile clients such as, for example, a personal digital assistant (PDA), laptop computer, pager, smart phone and the like, provided it includes sufficient processing capabilities.

Computer system 300 includes processing unit 301, system memory 302, and system bus 303 that couples various system components, including the system memory, to processing unit 301. Dual microprocessors and other multi-processor architectures also can be used as processing unit 301. System bus 303 may be any of several types of bus structure including a memory bus or memory controller, a peripheral bus, and a local bus using any of a variety of bus architectures. System memory 302 includes read only memory (ROM) 304 and random access memory (RAM) 305. A basic input/output system (BIOS) 306 can reside in ROM 304 containing the basic routines that help to transfer information among elements within computer system 300.

Computer system 300 can include a hard disk drive 307, magnetic disk drive 308, e.g., to read from or write to removable disk 309, and an optical disk drive 310, e.g., for reading CD-ROM disk 311 or to read from or write to other optical media. Hard disk drive 307, magnetic disk drive 308, and optical disk drive 310 are connected to system bus 303 by a hard disk drive interface 312, a magnetic disk drive interface 313, and an optical drive interface 314, respectively. The drives and their associated computer-readable media provide nonvolatile storage of data, data structures, and computer-executable instructions for computer system 300. Although the description of computer-readable media above refers to a hard disk, a removable magnetic disk and a CD, other types of media that are readable by a computer, such as magnetic cassettes, flash memory cards, digital video disks and the like, in a variety of forms, may also be used in the operating environment; further, any such media may contain computer-executable instructions for implementing one or more parts of the systems and method disclosed herein.

A number of program modules may be stored in drives and RAM 305, including operating system 315, one or more application programs 316, other program modules 317, and program data 318. The application programs and program data can include functions and methods programmed to acquire, process and display electrical data from one or more sensors, such as shown and described herein. The application programs and program data can include functions and methods programmed to process signals and compute a phase data as disclosed herein. The application programs and program data can also include functions and methods programmed to generate a cardiac singularity maps, corresponding composite singularity maps as well as other electrocardiographic maps as disclosed herein.

A user may enter commands and information into computer system 300 through one or more input devices 320, such as a pointing device (e.g., a mouse, touch screen), keyboard, microphone, joystick, game pad, scanner, and the like. For instance, the user can employ input device 320 to edit or modify a domain model. These and other input devices 320 are often connected to processing unit 301 through a corresponding port interface 322 that is coupled to the system bus, but may be connected by other interfaces, such as a parallel port, serial port, or universal serial bus (USB). One or more output devices 324 (e.g., display, a monitor, printer, projector, or other type of displaying device) is also connected to system bus 303 via interface 326, such as a video adapter.

Computer system 300 may operate in a networked environment using logical connections to one or more remote computers, such as remote computer 328. Remote computer 328 may be a workstation, computer system, router, peer device, or other common network node, and typically includes many or all the elements described relative to computer system 300. The logical connections, schematically indicated at 330, can include a local area network (LAN) and a wide area network (WAN).

When used in a LAN networking environment, computer system 300 can be connected to the local network through a network interface or adapter 332. When used in a WAN networking environment, computer system 300 can include a modem, or can be connected to a communications server on the LAN. The modem, which may be internal or external, can be connected to system bus 303 via an appropriate port interface. In a networked environment, application programs 316 or program data 318 depicted relative to computer system 300, or portions thereof, may be stored in a remote memory storage device 340.

What have been described above are examples. It is, of course, not possible to describe every conceivable combination of structures, components, or methods, but one of ordinary skill in the art will recognize that many further combinations and permutations are possible. Accordingly, the invention is intended to embrace all such alterations, modifications, and variations that fall within the scope of this application, including the appended claims.

Where the disclosure or claims recite "a," "an," "a first," or "another" element, or the equivalent thereof, it should be interpreted to include one or more than one such element, neither requiring nor excluding two or more such elements. As used herein, the term "includes" means includes but not limited to, and the term "including" means including but not limited to. The term "based on" means based at least in part on.

What is claimed is:

1. A non-transitory computer-readable medium having instructions executable by a processor, the instructions comprising:
 a composite map generator programmed to:
  receive a plurality of data sets including values computed for each of a plurality of points for a given spatial region of tissue, each of the plurality of datasets characterizes electrical information for each of the plurality of points for a different time interval;
  combine the values computed for each of a plurality of points over at least two different time intervals; and
  normalize the combined values relative to a common scale; and
 an output generator programmed to generate a composite map for the given spatial region based on the combined values that are normalized.

2. The medium of claim 1, wherein the output generator is further programmed to repeat the generating for a plurality of composite maps with increasing numbers of intervals until convergence criteria is satisfied for successive composite maps generated for the given spatial region.

3. The medium of claim 2, wherein the convergence is determined based on a correlation between the plurality of points of a previous composite map relative to the plurality of points of a next successive composite map.

4. The medium of claim 3, wherein the correlation is compared relative to a threshold to determine the convergence criteria has been satisfied.

5. The medium of claim 4, wherein the threshold is predefined or programmable in response to a user input.

6. The medium of claim 1, wherein the output generator is further programmed to generate a graphical map for each composite map and the first map, each of the graphical maps being presented in a successive order to demonstrate convergence of each singularity in the given spatial region.

7. The medium of claim 6, wherein the electrical information comprises a characteristic of a cardiac singularity computed by a singularity calculator for each of a plurality of points in the given spatial region.

8. The medium of claim 7, wherein the cardiac singularity comprises a phase singularity computed by the singularity calculator for each of the plurality of points in the given spatial region.

9. The medium of claim 1, wherein the given spatial region comprises one of an epicardial region or an endocardial region.

10. The medium of claim 1, wherein the given spatial region comprises a portion of a cardiac envelope or the entire cardiac envelope.

11. The medium of claim 1, wherein the values are computed based on electrical data acquired non-invasively for a patient.

12. The medium of claim 1, wherein the values are computed based on electrical data acquired invasively for the patient.

13. The medium of claim 1, wherein the combining the values comprises summing the values for each of the plurality of points from the at least two different time intervals.

14. A non-transitory computer-readable medium having instructions executable by a processor to perform a method comprising:
computing values for each of a plurality of points of a geometric surface in a first time interval of a plurality of time intervals and other values for each of the plurality of points of the geometric surface in a second time interval of the plurality of time intervals;
normalizing the values and the other values for each of the plurality of points of the geometric surface to a common scale;
aggregating the normalized values and the normalized other values into aggregated values,
generating a first composite map based on the aggregated values; and
repeating the computing, the normalizing, and the aggregating to generate at least another composite map that includes a respective value computed for each respective point of the plurality of points of the geometric surface until convergence criteria is satisfied for a plurality of successively generated composite maps for the geometric surface.

15. The medium of claim 14, wherein the aggregating comprises summing values for each respective point in the maps being aggregated.

16. The medium of claim 14, the method further comprising determining the convergence criteria is satisfied based on computing a correlation between the plurality of points of the geometric surface for each of the successively generated composite maps.

17. The medium of claim 16, the method further comprising comparing results of the computed correlation relative to a threshold to determine the convergence criteria has been satisfied for at least one singularity.

18. The medium of claim 17, wherein the threshold is predefined or programmable in response to a user input.

19. The medium of claim 14, the method further comprising generating a graphical map for each composite map and the first map, the graphical maps being presented in a successive order to demonstrate convergence visually for at least one singularity in the geometric surface.

20. The medium of claim 14, wherein the value computed for each of the plurality of points comprises a characteristic of a cardiac electrical singularity computed for each of the plurality of points in the surface.

21. The medium of claim 20, wherein the cardiac singularity comprises an electrical phase singularity computed for each of the plurality of points in the surface.

22. The medium of claim 14, wherein the geometric surface comprises one of an epicardial region or an endocardial region.

23. The medium of claim 14, wherein the geometric surface comprises a predefined portion of a cardiac surface or the entire cardiac surface.

24. The medium of claim 14, the method further comprising computing the values for each of the plurality points of the geometric surface based on electrical data acquired non-invasively for the patient.

25. The medium of claim 14, the method further comprising computing the values for each of the plurality points of the geometric surface based on electrical data acquired invasively for the patient.

26. The medium of claim 14, wherein the aggregating further comprises summing the values computed for each respective point of the plurality of points in the plurality of intervals.

27. The medium of claim 14, the method further comprising determining at least one parameter for delivering a therapy to a patient's heart based on at least one of the composite maps.

28. The medium of claim 27, wherein the therapy further comprising performing ablation at one or more sites determined based on at least one of the composite maps.

* * * * *